United States Patent
Drevik et al.

(10) Patent No.: US 6,629,965 B2
(45) Date of Patent: Oct. 7, 2003

(54) SANITARY NAPKIN

(75) Inventors: Solgun Drevik, Lindome (SE); Fredrik Asp, Onsala (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/006,665

(22) Filed: Dec. 10, 2001

(65) Prior Publication Data

US 2002/0087134 A1 Jul. 4, 2002

Related U.S. Application Data

(60) Provisional application No. 60/251,873, filed on Dec. 8, 2000.

(51) Int. Cl.[7] .................................................. A61F 13/15
(52) U.S. Cl. ............................. 604/385.01; 604/385.04
(58) Field of Search ....................... 604/385.01, 385.23, 604/385.04, 386, 358, 385.24, 385.27, 385.28

(56) References Cited

U.S. PATENT DOCUMENTS

| | | | | |
|---|---|---|---|---|
| 3,441,025 | A | * 4/1969 | Ralph | 128/289 |
| D234,162 | S | * 1/1975 | Kroyer | |
| 4,327,732 | A | * 5/1982 | Thinnes | 604/370 |
| 5,713,886 | A | * 2/1998 | Sturino | 604/390 |
| 5,807,365 | A | * 9/1998 | Luceri | 604/367 |
| 6,306,123 | B1 | * 10/2001 | Salerno et al. | 604/385.31 |
| 6,326,525 | B1 | * 12/2001 | Hamajima et al. | 604/378 |
| 6,410,822 | B1 | * 6/2002 | Mizutani | 604/380 |

FOREIGN PATENT DOCUMENTS

| | | | | |
|---|---|---|---|---|
| DE | 29614542 | * | 8/1996 | ........... A61F/13/15 |
| EP | 0 302 523 | | 2/1989 | |
| GB | 2 319 730 | A | 6/1998 | |
| JP | 10-5274 | | 1/1998 | |
| JP | 10-005274 | | 1/1998 | |
| SE | 502 419 | | 10/1995 | |
| WO | WO 90/04956 | | 5/1990 | |
| WO | WO 97/15259 | | 5/1997 | |
| WO | WO 98/51249 | * | 11/1998 | ........... A61F/13/15 |
| WO | WO 00/72790 | A1 * | 12/2000 | ........... A61F/13/15 |

* cited by examiner

Primary Examiner—Weilun Lo
Assistant Examiner—Jacqueline F Stephens
(74) Attorney, Agent, or Firm—Young & Thompson

(57) ABSTRACT

The present invention relates to an absorbent article (1) in the form of a sanitary napkin, a panty liner or a female incontinence napkin, comprising a front portion (2) and a rear portion (3) which includes an absorbent body (4, 5, 6) enclosed between a liquid-permeable casing sheet (7) and a liquid-impermeable casing sheet (8), wherein the absorbent body is comprised of a central pad (4) that extends from the forward end of the front portion to the rear end of the rear portion, and two side bodies (5, 6) which extend along the side edges of the central absorbent body on respective sides thereof and along a part of said body. According to the invention, the central absorbent body (4) tapers rearwardly from a section of greatest width located in the front portion (2) of the article to the end of the rear portion (3) of said article, wherein the side bodies (5, 6) extend rearwardly from a point on the tapering part of the central absorbent body to the rear end of the article.

16 Claims, 1 Drawing Sheet

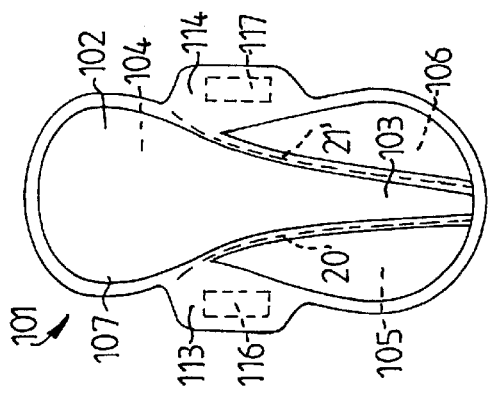
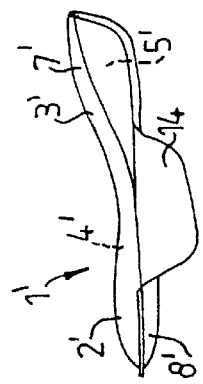
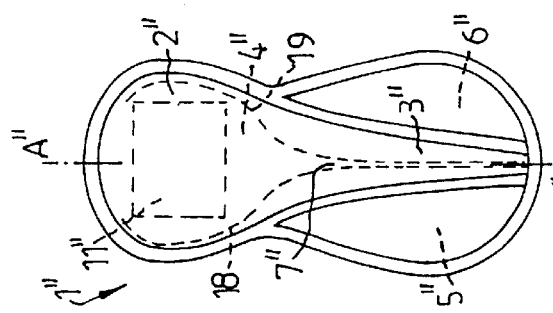
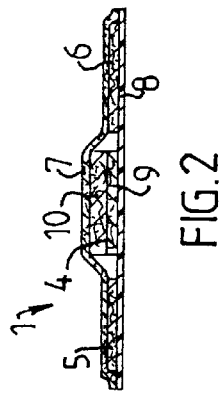
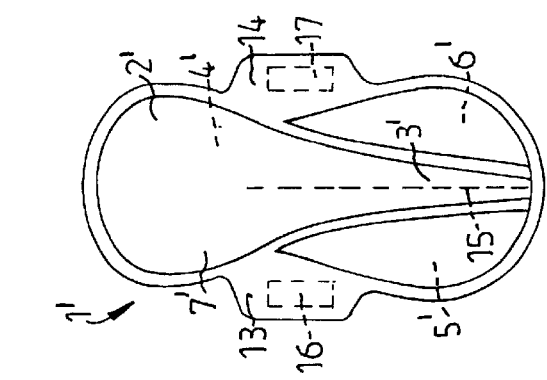
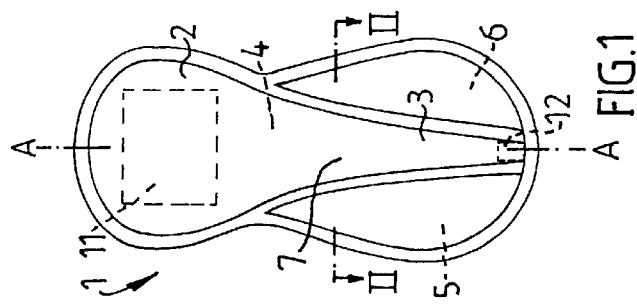

SANITARY NAPKIN

This application claims the benefit of U.S. Provisional Application No. 60/251,873, filed Dec. 8, 2000.

FIELD OF INVENTION

The present invention relates to an absorbent article, such as a sanitary napkin, a panty liner or a female incontinence napkin, wherein the article includes a front portion, a rear portion that includes an absorbent body enclosed between a liquid-permeable casing sheet and a liquid-impermeable casing sheet, and wherein the absorbent body comprises a central pad that extends from the front end of the front portion to the rear end of the rear portion, and two side bodies that extend along the side edges of the absorbent body along a part thereof and on respective sides thereof.

DESCRIPTION OF THE BACKGROUND ART

Sanitary napkins and similar articles often leak as a result of poor adaptation to the wearer's body or as a result of being displaced from their correct position during use. Many different solutions have been proposed with the intention of solving this problem. One method of adapting a sanitary napkin to the wearer's body is known from EP-A2-0 302 523, which teaches a sanitary napkin that has provided in the rear portion of the napkin an upwardly projecting ridge or hump which is intended to be placed between the wearer's buttocks and which has been produced by a sealed fold in said rear napkin portion. Another method is known from U.S. Pat. No. 5,197,959, which teaches a sanitary napkin that includes a spring-back element placed beneath an absorbent body, said element imparting an upwardly convex cross-sectional shape to the absorbent body in use.

W 97/15259 teaches a sanitary napkin of the kind defined in the introduction, in which centrally located side bodies impart an upwardly convex shape to the absorbent body in a longitudinal central part thereof, by virtue of elastic means. A sanitary napkin of this kind functions well under the majority of conditions. Rearward leakage can occur, however, when the wearer lies on her back.

An object of the present invention is to provide an absorbent article in the form of a sanitary napkin, a panty liner or a female incontinence napkin that conforms effectively to the wearer's body, has good leakage security even in respect of rearward leakage, and that can be produced and packaged in a flat state.

SUMMARY OF THE INVENTION

These objects are achieved with an absorbent article in the form of a sanitary napkin, a panty liner or a female incontinence napkin that has a front portion and a rear portion and which includes an absorbent body enclosed between a liquid-permeable casing sheet and a liquid-impermeable casing sheet, wherein the absorbent body comprises a central pad that extends from the front end of the front portion to the rear end of the rear portion, and two side bodies that extend along the side edges of the central absorbent body on respective sides thereof and along a part of said absorbent body, characterised in that the central absorbent body narrows rearwardly from a section of greatest width in the front portion to the end of the rear portion; and in that the side bodies extend rearwardly from a point on the tapering part of the central absorbent body that is located in the front part of the rear end of the article. Because the central absorbent body tapers or narrows rearwardly, it will fit effectively in the space between the wearer's buttocks and obtain good abutment with the wearer's body along its full length. This provides an effective seal against rearward leakage. The side bodies will, at the same time, lie against the wearer's buttocks and therewith ensure an effective seal against lateral leakage at the rear portion of the article.

In one preferred embodiment, the side bodies consist of bodies that are separate from the central absorbent body. The central absorbent body has a greatest width of 90–60 mm, preferably 70 mm, in the front portion of the article, and a smallest width of 5–15 mm, preferably 10 mm, in the rear portion of said article. The central absorbent body also includes a first layer of absorbent material of high absorbency, and a second layer of liquid acquisition material disposed between the first layer of absorbent material and the liquid-permeable casing sheet. The side bodies may conveniently consist of the same material as the liquid acquisition sheet or the first sheet of absorbent material.

In a second advantageous embodiment, a pretensioned elastic element extends along the longitudinal symmetry axis of the article, from the rear end of said article to its front portion. The elastic element preferably extends into the front portion of said article. The elastic element is suitably disposed between the central absorbent body and the liquid-permeable casing sheet.

An elastic element may also be disposed in the intermediate spaces between the central absorbent body and the side bodies between the casing sheets.

When the central absorbent body includes first layers of absorbent material of high absorbency, and a second layer of liquid acquisition material disposed between the first layer of absorbent material and the liquid-permeable casing sheet, the pretensioned elastic element will preferably be disposed on that side of the first layer of absorbent material of the central absorbent body that lies distal to the liquid-impermeable casing sheet and fastened to said layer.

In one advantageous variant, the pretensioned elastic element may extend longitudinally over the whole of the central absorbent body and in the front portion of the article extend along the side edges of said front portion.

In one variant of the embodiments, the side bodies may constitute parts of a layer of absorbent material included in the central absorbent body, wherewith the side bodies are conveniently delimited from the central absorbent body by fold lines in the layer of which the side bodies form part.

BRIEF DESCRIPTION OF THE DRAWING

The invention will now be described with reference to the accompanying drawing, in which FIG. 1 is a plan view of a first embodiment of an inventive sanitary napkin;

FIG. 2 is a cross-sectional view taken on the line 11—11 in FIG. 1;

FIGS. 3 and 4 are respectively a plan view and a side view of a second embodiment of an inventive sanitary napkin; and FIGS. 5 and 6 are respectively a plan view of a sanitary napkin according to a third and a fourth embodiment of the invention.

DESCRIPTION OF EMBODIMENTS

FIGS. 1 and 2 illustrate schematically a disposable sanitary napkin 1 according to a first embodiment of the invention. The napkin 1 has a front portion 2, a rear portion 3, a central absorbent body 4 and two side bodies 5, 6 comprised of absorbent material and essentially located in the rear portion 3 of the napkin. The central absorbent body 4 and the side bodies 5, 6 are enclosed between a liquid-permeable casing sheet 7 and a liquid-impermeable casing sheet 8. The casing sheets 7, 8 protrude beyond the absorbent bodies 4–6 around the full perimeter of the napkin, and are joined together, i.e. welded or glued, at those portions that lie outside the absorbent bodies.

The central absorbent body 4 includes a first layer 9 of absorbent material of high absorbency. This material will preferably be capable of absorbing 9 g liquid per g of absorbent material. The central absorbent body also includes a second layer 10 of material that has good liquid acquisition properties, i.e. a material that is capable of acquiring liquid quickly and storing said liquid temporarily. The acquisition layer 10 is disposed proximal to the liquid permeable casing sheet 7. As a result of this construction, the absorbent body ensures that liquid discharged onto the liquid-permeable casing sheet 7 will be transported rapidly therefrom and taken into the layer 10. The layer 10 is drained by the layer 9 by capillary forces. In order for drainage to take place, it is necessary that the capillaries of the layer 9 are smaller than the capillaries of the layer 10. With the intention of reducing the risk of re-wetting, particles of so-called super-absorbent material may conveniently be included, i.e. polymers that are able to absorb liquid in quantities corresponding to several times the weight of the polymer particles mixed in the layer.

The central absorbent body 4 will conveniently have a length of 140–260 mm. The absorbent body has a greatest width of 90–60 mm, preferably 70 mm, in the front portion of the article and narrows rearwardly from said front portion to the rear end of the rear portion, in which it has a smallest width of 5–15 mm, preferably 10 mm. This configuration is well adapted to the wearer's body shape, by virtue of the fact that the rear portion of the absorbent body 4 fits into the space between the wearer's buttocks. The absorbent body 4 may be relatively rigid as a result of this construction, without being felt to be uncomfortable due to the fact that the clamping forces exerted by the wearer's thighs will be taken-up by curvature of the absorbent body. The reaction forces exerted against the thighs with such curving of the absorbent body are small, meaning that the described napkin will be felt comfortable to wear. Such curving of the absorbent body is also beneficial from an absorption aspect, since the napkin is thereby pressed into tight abutment with the wearer's body within the wetting range. The form and the dimensions of the described absorbent 4 thus enables a relatively rigid absorbent body to be used with no adverse affects with regard to function and comfort. When the napkin is in use, the front portion of the absorbent body will bend around the labia, meaning that the edges of the front portion will be unable to chafe against the wearer's skin. The stiffness of the absorbent body 4 is determined by the stiffness of the layer 9. In order to ensure that the rear edge of the layer 9 will not chafe against the wearer's skin, the layer 10 is conveniently extended beyond the layer 9 in the rear end part of the absorbent body through a distance of 20–30 mm in the case of the illustrated embodiment.

The sanitary napkin 1 also includes an adhesive coating 11 on the outside of the liquid-impermeable casing sheet 8 in the front portion 2 of the napkin. In use, this adhesive layer will fasten to the inner surface of the wearer's panties or underpants. Prior to use, the adhesive coating 11 is covered with a protective layer of release paper, for instance. A friction coating 12 may also be disposed on the outer surface of the casing sheet 8, within the region of the rear portion of the central absorbent body. It is also possible to use mechanical fasteners, such as touch-and-close fastener elements or other types of hook elements that can co-act with the textile material from which panties and underpants are normally made. It is also feasible to use solely friction coatings that have a high coefficient of friction against textile material, such as certain foamed materials, or combinations of the aforesaid fastener means.

When using the sanitary napkin 1 described with reference to FIGS. 1 and 2, the napkin is fastened to the inner surface of a pair of panties or pants, whereafter the panties are pulled up against the wearers body, wherewith the rear portion of the absorbent body 4 is pressed in between the wearer's buttocks. Because the side bodies 5, 6 are separate parts, they are able to swing freely in relation to the absorbent body around natural pivot means formed by the interspace between the outer edges of the absorbent body 4 and the inner edges of the side bodies, said side bodies being swung down and pressed into abutment with the buttocks of the wearer by the donned panties.

The liquid-permeable casing sheet 7 is comprised of a soft skin-friendly material. This outer sheet, or top sheet, may be comprised of one of a number of different types of non-woven material. Other materials that can be used include perforated plastic film, plastic net, knitted, crocheted or woven textiles, and combinations and laminates of such types of material. The plastic may be a thermoplastic, e.g. polyethylene (PE). The non-woven material may consist of natural fibres, such as cellulose or cotton, although it may alternatively consist of synthetic fibres, such as polyethylene (PE), polypropylene (PP), polyurethane (PU), a polyester, nylon or regenerated cellulose, or a mixture of different fibres. All materials that are used to provide a liquid-permeable top sheet in absorbent articles, such as sanitary napkins, panty liners or incontinence napkins can be used for the liquid-permeable casing sheet 7 and it will be understood that the material recited above is given by way of example only.

The liquid-impermeable casing sheet 8 consists of a flexible material, preferably a thin plastic film of polyethylene (PE), polypropylene (PP) or a polyester, but may alternatively consist of a laminate of a liquid-permeable material, such as non-woven material, and a liquid-impermeable material. All materials that are used as liquid-impermeable outer sheets, or backing sheets, in the production of absorbent articles may be used. The casing sheet 8 may beneficially be air-permeable.

The absorbent layer 9 in the absorbent body 1 may be comprised of a dry-formed cellulose fibre material that has been compressed to a density of at least 250 g/dm$^3$, preferably to a density of 300–400 g/dm$^3$ without subsequent defibration and fluffing. Such a material is known from WO 94/10956, to which reference is made for further information concerning the method of manufacture and properties of such material. It will be pointed out, however, Do that such material also has good liquid retention properties. The layer 9 will also suitably have a weight per unit area of 200–600 g/m$^2$, preferably 250–400 g/m$^2$, which results in a layer that is not thicker than 1.5 mm. The layer 9 may also be comprised of a hard compressed, mat-formed or air-laid fluff pulp, preferably chemothermomechanical fluff pulp (CTMP) of corresponding density and weight per unit area. Such a material may have a stiffness of about 5.5 N measured in accordance with a CIRCULAR BEND PROCEDURE described in EP-A-0 336 578, to which reference is made for further information.

The material of good liquid acquisition properties used in the layer 10 may be a wad of cellulose fibres, synthetic fibres or mixtures thereof. The presence of such a layer reduces the risk of discharged liquid running on the surface of the napkin, reaching the edge of the napkin, and then staining the wearer's panties or other clothing. Although the layer 9 itself has good liquid acquisition properties, it can be suitable to provide a liquid acquisition layer in the narrow part of the napkin in particular. The layer 10 is suitably comprised of LDA pulp (Low Density Airlaid). The LDA pulp may be a chemical pulp, mechanical pulp or a mixture of such pulps, preferably with a binding fibre admixture. The layer 10 may alternatively be comprised of carded spunlace. The layer 10 will preferably have a density of about 0.05 g/cm$^3$ and a weight per unit area of between 20–150 g/m$^2$.

The side bodies 5, 6 may conveniently be made of the same material as the layer 9 or the layer 10. Because the primary purpose of the side bodies is to prevent side leakage, they will not need to take-up large quantities of liquid, meaning that all materials that are included in absorbent articles can be used in the side bodies.

The adhesive used in the coating 11 may comprise a pressure-sensitive hotmelt glue, e.g. Ecomelt H145 from Collano, Switzerland. Alternatively, there may be used other commercially available pressure-sensitive adhesives, including adhesives that are pressure-sensitive in a cold state, such as acrylate glue, normally combined with adhesive-enhancing additives, such as terpene resin, or hotmelt glue, such as styrene and butadiene copolymers.

FIGS. 3 and 4 illustrate a second embodiment of an inventive sanitary napkin, here referenced 1'. The sole difference between the napkin 1' and the napkin 1 shown in FIGS. 1 and 2 is that the napkin 1' is provided with flaps 13, 14 and a pretensioned elastic element 15. Those components of the napkin 1' that find correspondence in the napkin 1 have been identified by the same reference signs as those used in FIGS. 1 and 2 with the addition of a prime. Accordingly, the description of the embodiment illustrated in FIGS. 3 and 4 is limited to the aforesaid differences and reference is made to the embodiment shown in FIGS. 1 and 2 in other respects.

As before mentioned, the napkin 1' includes flaps 13, 14, which extend laterally beyond the absorbent body 4' and the side bodies 5', 6' in the midway part of the napkin as seen in its longitudinal direction. When the napkin is worn, these flaps are intended to be folded around the side edges of the wearer's underpants and fastened to the outer surface thereof. The flaps 13, 14 are provided to this end with adhesive coatings 16, 17 of the same type as the coating 11 on the napkin 1. The flaps conveniently consist of laterally extending portions of the casing layers 7', 8', but may alternatively consist of separate flexible parts.

The napkin 1' also includes an elastic element 15 in the form of one or more elastic threads or an elastic ribbon extending along the longitudinal symmetry axis of the napkin from its rear end and slightly into the front portion 2' of the napkin. The elastic element 15 is preferably disposed between the first layer 9' of the absorbent body 4' and the liquid-permeable casing sheet 7', either between the first layer 9' and the second layer 10' or between the layer 10' and the casing sheet 7', and fastened appropriately to the casing sheet or to the first layer 9' in a pretensioned state. For instance, the elastic element 15 may be comprised of an elastic ribbon disposed between two layers of inelastic material, wherewith the element is fastened directly to one or two of said layers. Alternatively, the elastic element 15 may be comprised of one or more elastic threads that are fastened directly to the casing layer 7' or to the layer 9' or disposed between a strip of inelastic material that is disposed to this end between the threads and surrounding layer, wherewith the strip and either the casing sheet or the layer 9' are fastened to each other and to the intermediate thread.

The elastic element 15 causes the rear portion of the absorbent body 4' to bend or curve so as to impart to the napkin the three-dimensional shape shown in FIG. 4 when not subjected to load. This means that the rear portion of the absorbent body 4' will be pressed into resilient abutment with the wearer's body subsequent to donning the napkin 1'. This obviates the need for a friction coating on the rear part of the napkin. The elastic element 15 provides an improved body fit and leakage security of the napkin 1' in comparison with the embodiment of the napkin 1 shown in FIGS. 1 and 2.

FIG. 5 illustrates a third embodiment of the inventive napkin, here referenced 1". The sole difference between the napkin 1" and the napkin 1 shown in FIGS. 1 and 2 is that the napkin 1" includes a pretensioned elastic element 18, 19. Those components of the napkin 1" that find correspondence in the napkin 1 have been given the same reference signs as those used in FIGS. 1 and 2, with the addition of a double prime. The following description of the FIG. 5 embodiment is limited to the aforesaid differences and reference is made to the description of the embodiment shown in FIGS. 1 and 2 in other respects.

The pretensioned elastic element is comprised of two elastic threads 18, 19 that extend longitudinally across the whole of the central absorbent body 4". The two threads 18, 19 extend in the rear portion 3" of the napkin along the longitudinal symmetry axis A"–A" of the napkin, while in the front portion 2" of the napkin said threads extend along the side edges of the central absorbent body. Moreover, the threads 18, 19 are disposed between the layers 9", 10" of the central absorbent body and are fastened at least to the stiffer layer 9". The threads 18, 19 located in the front portion of the napkin causes this napkin portion to be deformed into a basin-like shape. Each of the threads 18, 19 may consist of several is elastic filaments and also of elastic ribbons.

FIG. 6 illustrates a sanitary napkin 101 according to a further embodiment. The sole difference between the napkin 101 and the napkin 1' shown in FIGS. 3 and 4 resides in the design of the pretensioned elastic element 20, 21. Those components of the napkin 101 that find correspondence in the napkin 1' have been given the same reference numerals as those used in FIGS. 3 and 4 with the addition of 100. Accordingly, a description of the FIG. 6 embodiment is limited to the aforesaid difference and reference is made to the embodiment shown in FIGS. 3 and 4 in other respects.

The pretensioned elastic element 20, 21 is comprised of two elastic threads disposed between the casing sheets 107, 108 in the interspaces between the central absorption body 104 and the side bodies 105, 106, and extending from the rear edge of the napkin into the front napkin portion 104. The threads 20, 21 may consist of one or more elastic filaments or ribbons.

The sanitary napkins, according to the aforedescribed embodiments, ensure good security against rearward leakage due to the fact that their rear portions connect extremely well with the wearer's body. The rear portion of the central absorbent body functions as a seal to prevent rearward running of liquid, while the side bodies manage liquid that runs off the tapering part of the central absorbent body in a transverse direction, nd also form an absorption reserve of backup for draining the central absorbent body should said body become saturated. Moreover, these napkins have a flat shape, i.e. side bodies and the central absorbent body are flat and are not deformed per se during manufacture and packaging, which facilitates both manufacture and packaging at the same time as the packaged napkins will take up less space than if they had been given the three-dimensional shape desired in use already in the manufacturing stage.

It will be understood that the described and illustrated exemplifying embodiments can be modified within the scope of the invention. For instance, the napkin 1 may be provided with flaps corresponding to the flaps 13, 14 of the napkin 1', and the elastic element 15 may be disposed on the liquid-permeable casing sheet even though this is not preferred. Furthermore, the side bodies may be made of the same material as one layer of the central absorbent body and may even form a part of this layer, said part being separated from the central absorbent body by fold lines that extend along the contour of the layer proximal to the liquid-impermeable casing sheet. It is not always necessary to provide a friction coating on a sanitary napkin that lacks an elastic element, as the pressure force exerted by the wearer's underpants is often sufficient to hold a donned napkin in place. Neither is it necessary for the central absorbent body to include a liquid acquisition layer, as this body may be comprised of one single layer. It is also possible for the central absorbent body to include more than two layers, for instance to include a liquid dispersion layer between the liquid acquisition layer and the liquid storage layer. A layer of superabsorbent particles may also be disposed proximal to the liquid-impermeable casing sheet. The described elastic element features may also be combined with one another. For instance, the napkin illustrated in FIG. 3 may be provided with elastic threads in the interspace between the central absorbent body and the side bodies. Moreover, the flap-equipped napkins may also be provided with adhesive fastener devices on the outer surface of the liquid-impermeable layer or sheet in the same way as the napkin shown in FIG. 1. The invention is therefore limited solely by the contents of the accompanying Claims.

What is claimed is:

1. An absorbent article selected from the group consisting of a sanitary napkin, a panty liner and a female incontinence napkin, the article comprising:

a front portion, a rear portion, an absorbent body enclosed between a liquid-permeable casing sheet, which in use is intended to face a wearer's body, and a liquid-impermeable casing sheet intended to face away from the wearer's body;

said absorbent body comprising a central pad that extends from a front end of the front portion to a rearmost edge of the rear portion;

two side bodies which extend along side edges of the absorbent body and along a part of said absorbent body on respective sides thereof;

said absorbent body narrowing rearwardly from a section of greatest width located in the front portion to the rearmost edge of the rear portion;

said side bodies extending rearwardly from a point on a tapering part of the absorbent body and terminating at the rearmost edge of the rear portion, whereby during use of the absorbent article, the side bodies abut the wearer's buttocks.

2. The absorbent article according to claim 1, wherein the side bodies consist of bodies that are separate from the absorbent body.

3. The absorbent article according to claim 1, wherein the side bodies consist of parts of a layer of absorbent material included in the absorbent body.

4. The absorbent article according to claim 3, wherein the side bodies are delimited from the absorbent body by fold lines in that layer of which the side bodies form parts.

5. The absorbent article according to claim 1, wherein the absorbent body has a greatest width of 90–60 mm in the front portion, and a smallest width of 5–15 mm in the rear portion.

6. The absorbent article according to claim 5, wherein the absorbent body has a greatest width of 70 mm in the front portion and a smallest width of 10 mm in the rear portion.

7. The absorbent article according to claim 1, further comprising a pretensioned elastic element that extends along a longitudinal symmetry axis of the article from the rearmost edge to said front portion.

8. The absorbent article according to claim 7, wherein the elastic element is disposed between the absorbent body and the liquid-permeable casing sheet.

9. The absorbent article according to claim 8, wherein the pretensioned elastic element is disposed on that side of the first layer of absorbent material of the absorbent body that is distal from the liquid-impermeable casing sheet and is fastened to said first layer.

10. The absorbent article according to claim 7, wherein the elastic element extends into the front portion.

11. The absorbent article according to claim 7, wherein the pretensioned elastic element extends longitudinally along the whole of the absorbent body, and in the front portion of the article extends along side edges of said front portion.

12. The absorbent article according to claim 1, further comprising a pretensioned elastic element disposed in an interspace between the absorbent body and the side bodies between the casing sheets.

13. The absorbent article according to claim 1, wherein the absorbent body includes a first layer of absorbent material of high absorbency and a second layer of liquid acquisition material disposed between the first layer of absorbent material and the liquid-permeable casing sheet.

14. The absorbent article according to claim 13, wherein the side bodies are comprised of the same material as the first layer of absorbent material of high absorbency.

15. The absorbent article according to claim 14, wherein the pretensioned elastic element extends longitudinally along the whole of the absorbent body, and in the front portion of the article extends along side edges of said front portion.

16. The absorbent article according to claim 13, wherein the side bodies are comprised of the same material as the second layer of liquid acquisition material.

* * * * *